(12) United States Patent
Pipenhagen et al.

(10) Patent No.: US 9,408,595 B2
(45) Date of Patent: Aug. 9, 2016

(54) MONORAIL SYSTEM FOR VASCULAR CLOSURE DEVICE AND METHODS

(75) Inventors: Catherine A. Pipenhagen, Chanhassen, MN (US); Valerie J. Glazier, Eden Prairie, MN (US); Scott A. Kramer, Minneapolis, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 0 days.

(21) Appl. No.: 13/392,750

(22) PCT Filed: Aug. 30, 2010

(86) PCT No.: PCT/US2010/002375
§ 371 (c)(1),
(2), (4) Date: Mar. 15, 2012

(87) PCT Pub. No.: WO2011/025543
PCT Pub. Date: Mar. 3, 2011

(65) Prior Publication Data
US 2012/0165854 A1 Jun. 28, 2012

Related U.S. Application Data

(60) Provisional application No. 61/238,385, filed on Aug. 31, 2009.

(51) Int. Cl.
*A61B 17/08* (2006.01)
*A61B 17/00* (2006.01)
*A61M 25/01* (2006.01)

(52) U.S. Cl.
CPC .... *A61B 17/0057* (2013.01); *A61M 2025/0183* (2013.01)

(58) Field of Classification Search
CPC ................... A61B 17/0057; A61M 2025/0183
USPC ................................................... 606/213, 191
See application file for complete search history.

(56) References Cited

U.S. PATENT DOCUMENTS

| 5,179,963 A | 1/1993 | Berger |
| 5,486,195 A * | 1/1996 | Myers et al. ............... 606/213 |

(Continued)

FOREIGN PATENT DOCUMENTS

| WO | 0156645 A1 | 8/2001 |
| WO | 02062234 A2 | 8/2002 |

(Continued)

OTHER PUBLICATIONS

U.S. Appl. No. 61/238,297, filed Aug. 31, 2009, for "Compressible Arteriotomy Locator for Vascular Closure Devices and Methods."

(Continued)

*Primary Examiner* — Corrine McDermott
*Assistant Examiner* — Sarah Simpson
(74) *Attorney, Agent, or Firm* — Holland & Hart

(57) ABSTRACT

A tissue puncture closure assembly including a wire assembly and first and second devices. The wire assembly includes a first wire member and a second wire member that each include a distal end portion and a proximal end portion. At least portions of the second wire member are arranged side-by-side with the first wire member. The distal end portion of the first wire member is connected to the distal end portion of the second wire member, and a proximal end portion of the first wire member is disconnected from the proximal end portion of the second wire member. The first device is operable to advance over the first wire member. The second device is operable to advance over the second wire member.

17 Claims, 8 Drawing Sheets

(56) References Cited

U.S. PATENT DOCUMENTS

| | | | |
|---|---|---|---|
| 6,045,569 A | 4/2000 | Kensey et al. | |
| 6,090,130 A | 7/2000 | Nash et al. | |
| 6,569,151 B1 * | 5/2003 | Nash et al. | A61M 25/00 604/103 |
| 6,699,262 B2 * | 3/2004 | Redmond et al. | 606/213 |
| 7,083,635 B2 * | 8/2006 | Ginn | 606/213 |
| 2005/0131459 A1 * | 6/2005 | Akerfeldt | 606/214 |

FOREIGN PATENT DOCUMENTS

| | | |
|---|---|---|
| WO | 2005110280 A2 | 11/2005 |
| WO | 2006032686 A1 | 3/2006 |

OTHER PUBLICATIONS

PCT International Search Report for International Application No. PCT/US2010/002375, mailed Mar. 4, 2011.

* cited by examiner

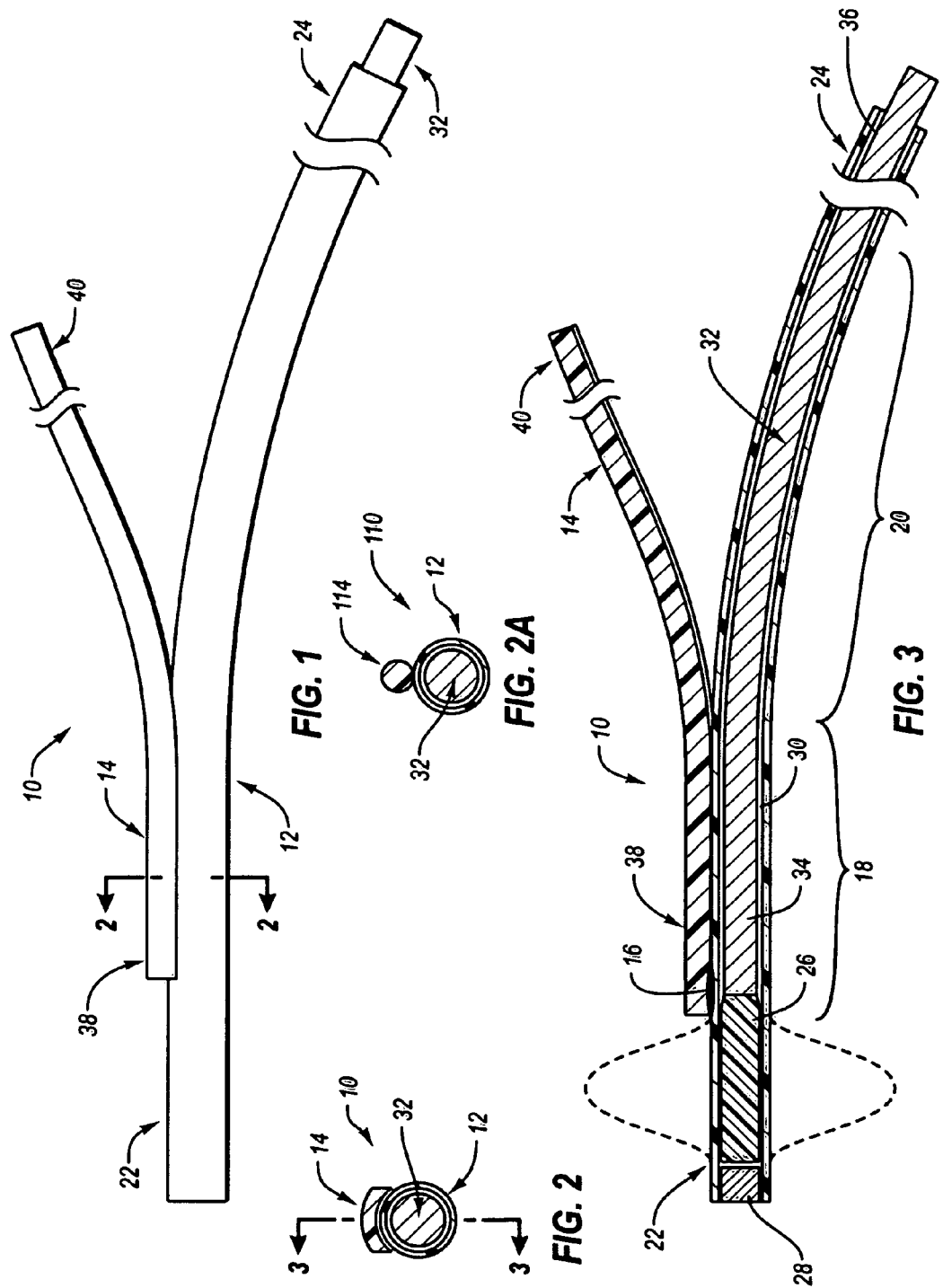

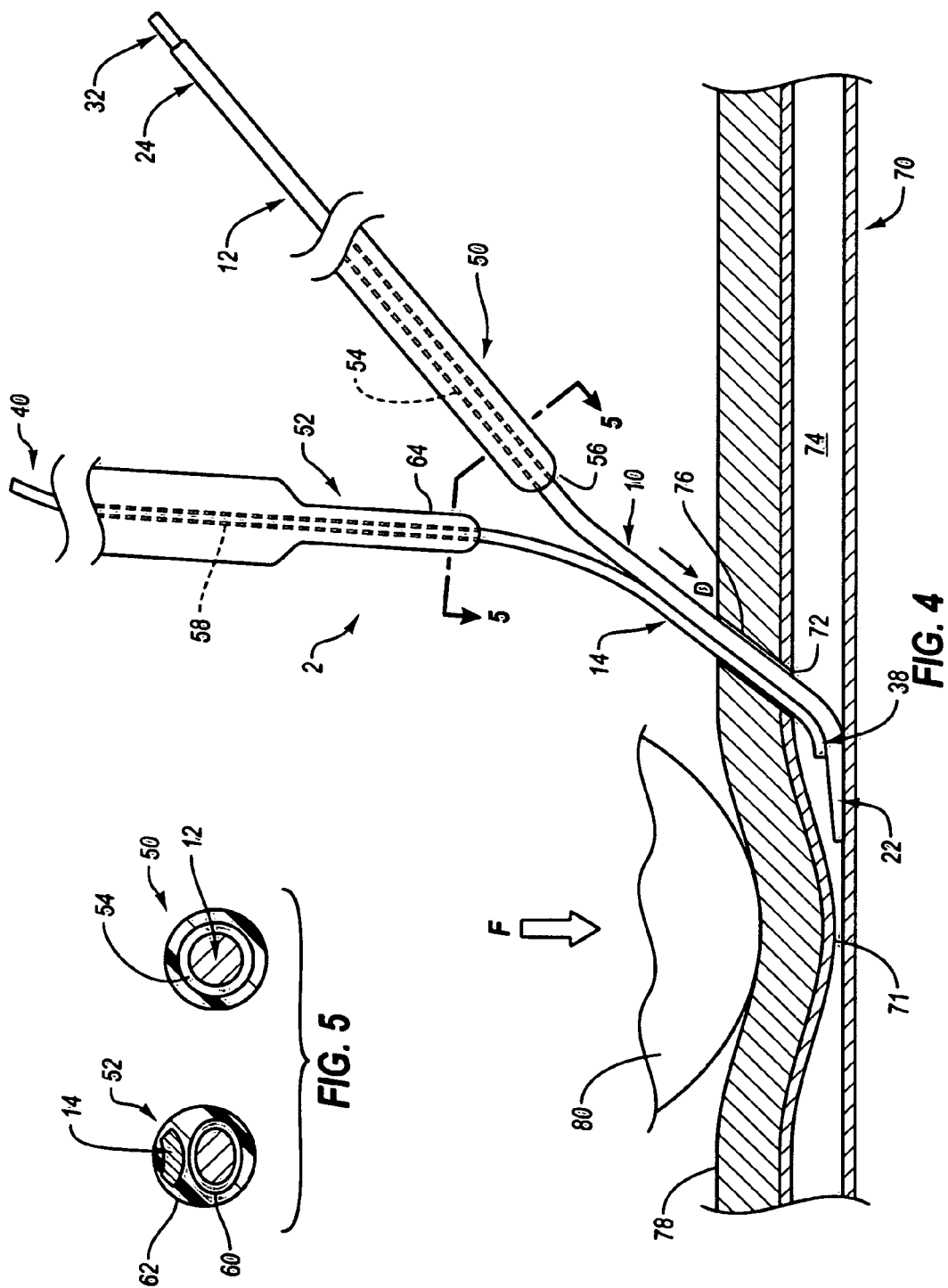

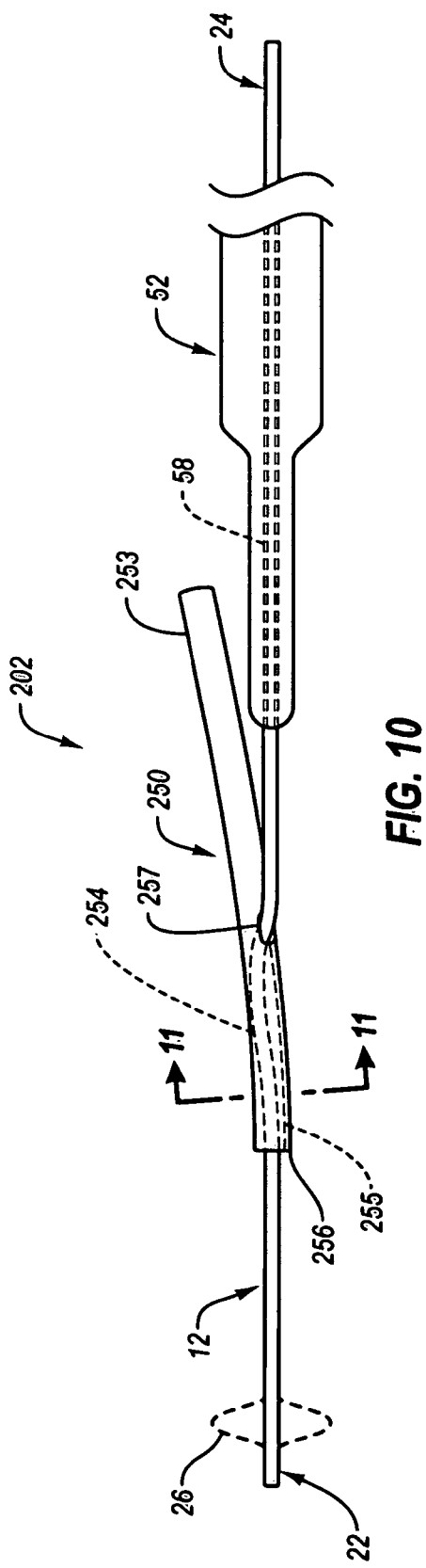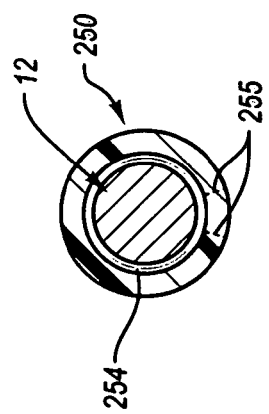
FIG. 10
FIG. 11

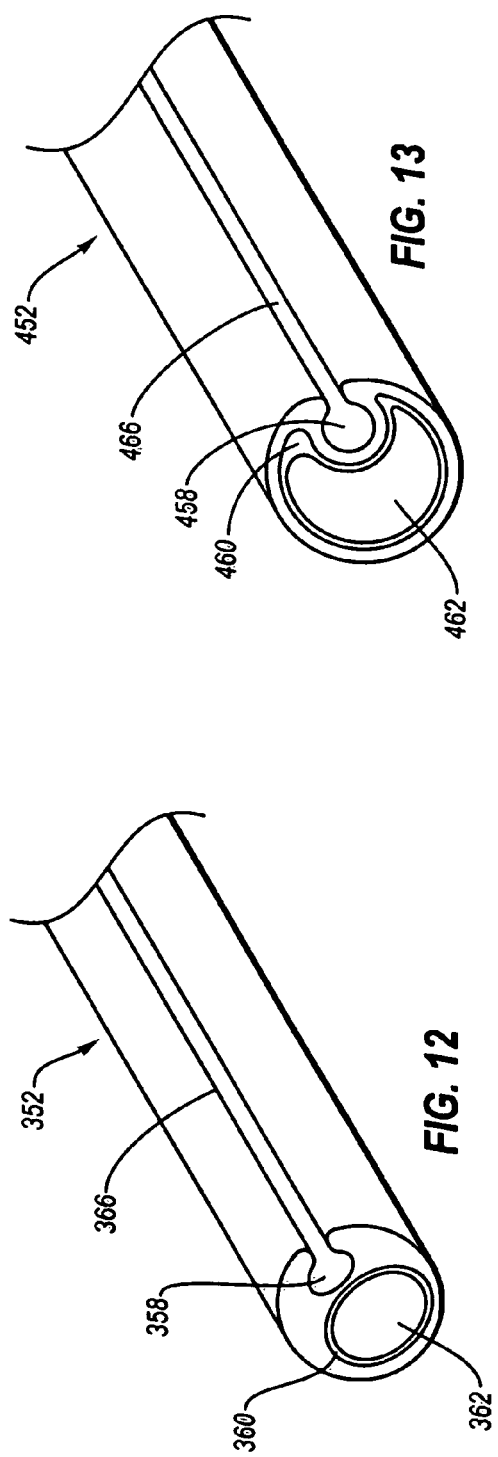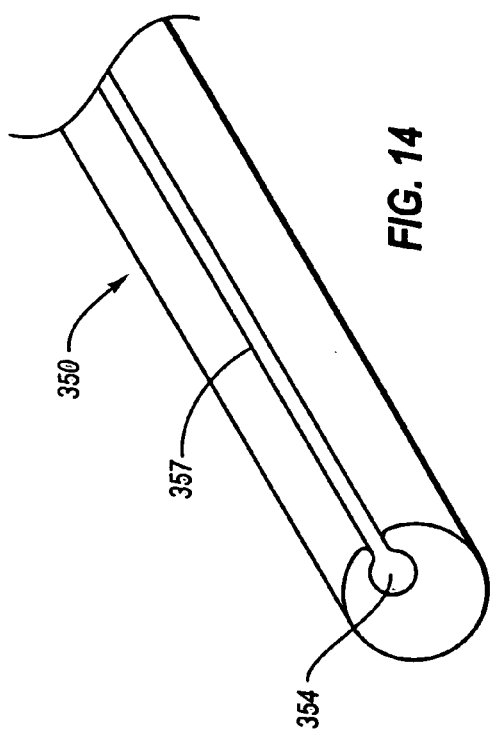

MONORAIL SYSTEM FOR VASCULAR CLOSURE DEVICE AND METHODS

RELATED APPLICATION

This application claims the benefit of U.S. Provisional Patent Application No. 61/238,385, filed Aug. 31, 2009, which is hereby incorporated by reference herein in its entirety.

TECHNICAL FIELD

The present disclosure relates generally to medical devices and more particularly to vascular closure devices.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., a catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, may be stopped by utilizing vascular closure devices, such as those described in U.S. Pat. Nos. 6,090,130 and 6,045,569, which are hereby incorporated in their entireties by this reference.

Typical closure devices such as the ones described in the above-mentioned patents place a sealing plug at the tissue puncture site. Successful deployment of the sealing plug involves ejecting the sealing plug from within the closure device sheath to a location in alignment with and adjacent to the tissue puncture along an outer surface of the vessel and within a percutaneous tissue tract. In some applications, a dilator is used to expand the tissue tract prior to inserting the closure device into the tissue tract and ejecting the sealing plug adjacent to the tissue puncture. The dilator is advanced over a guidewire that has been previously advanced through the tissue tract and tissue puncture. After dilating the tissue tract, the dilator is retracted off from the guidewire and the closure device is advanced over the guidewire to the tissue tract where the sealing plug is ejected. Mounting the dilator and closure device to the guidewire and later advancing and retracting the dilator and closure device along the guidewire typically requires both of the operator's hands. In at least some treatment procedures, one of the operator's hands is needed to apply pressure to the patient adjacent to the tissue puncture to provide hemostasis and hold the guidewire within the vessel.

SUMMARY

One aspect of the present disclosure relates a tissue puncture closure assembly that includes a wire assembly and first and second devices. The wire assembly includes a first wire member and a second wire member. The first wire member has a distal end portion and a proximal end portion. The second wire member has a distal end portion and a proximal end portion, wherein at least portions of the second wire member are arranged side-by-side with the first wire member. The distal end portion of the first wire member is connected to the distal end portion of the second wire member, and a proximal end portion of the first wire member is disconnected from the proximal end portion of the second wire member. The first device is configured to advance over the first wire member. The second device is configured to advance over the second wire member.

The first device may be a tissue closure device and the second device may be a dilator. The first wire member has a first cross-sectional shape and the second wire member has a second cross-sectional shape that may be different from the first cross-sectional shape. One of the first and second wire members may include an expandable anchor positioned at the distal end portion thereof, and an actuator member that extends from the anchor to the proximal end portion of thereof. The actuator member may be operable to move the anchor between expanded and unexpanded states. The first device may include a sealing pad and is operable to position the sealing pad within a percutaneous incision. The first device may include a first wire lumen and a sealing pad lumen, the sealing pad lumen may be radially spaced apart from the first wire lumen, and the second device may include a second wire lumen. The first and second wire lumens may be configured to house the first and second wire members, respectively.

Another aspect of the present disclosure relates to a tissue puncture closure assembly that is adapted for insertion into and sealing of a tissue puncture in an internal tissue wall that is accessible through a percutaneous incision. The device includes a guidewire, a closure device and a dilator. The guidewire has a distal end and a proximal end. The distal end extends through the tissue puncture and percutaneous incision, and the proximal end is spaced proximal of the percutaneous incision. The closure device includes a sealing pad and a first guidewire lumen. A portion of the guidewire extends through the first guidewire lumen. The dilator includes a second guidewire lumen, and a portion of the guidewire extends through the second guidewire lumen. The closure device and the dilator are operable to advance over the guidewire for use within the percutaneous incision without retracting the closure device and dilator from the proximal end of the guidewire.

The closure device and the dilator may be operable to advance over the guidewire sequentially for use within the percutaneous incision. The guidewire may include first and second guidewire portions arranged side-by-side, wherein the first wire portion extends through the first guidewire lumen and the second guidewire portion extends through the second guidewire lumen. The first and second guidewire portions may have different cross-sectional shapes. The guidewire may include an expandable anchor portion. The closure device may further include a sealing pad lumen arranged adjacent to the first guidewire lumen, wherein the sealing pad is positioned within the sealing pad lumen. The second guidewire lumen may be configured to have a closed state and an open state, wherein in the closed state the guidewire is retained within the dilator, and in the open state the guidewire is removable from the dilator prior to retracting the dilator from the proximal end of the guidewire.

Another aspect of the present disclosure relates to a method of sealing a tissue puncture in an internal tissue wall that is accessible through a percutaneous incision. The method includes providing a closure device, a dilator, and a guidewire, the closure device including a sealing pad. The method further includes advancing a distal end of the guidewire through the percutaneous incision and the tissue puncture, advancing the dilator over the guidewire to dilate the percutaneous incision, retracting the dilator out of the percutaneous incision, and advancing the closure device over the guidewire to position the sealing pad within the percutaneous incision without retracting the dilator off a proximal end of the guidewire.

The guidewire may include first and second guidewire members arranged side-by-side and connected to each other at distal ends of the first and second guidewire members, advancing the dilator may include advancing the dilator over the first guidewire member, and advancing the closure device may include advancing the closure device over the second guidewire member. Advancing the distal end of the guidewire may include arranging portions of the first and second guidewire members that are positioned within the percutaneous incision adjacent to each other, and arranging portions of the first and second guidewire members that are proximal of the percutaneous incision spaced apart from each other. The method may further include removing the dilator from the guidewire in a lateral direction while the dilator is spaced distal of the proximal end of the guidewire. The closure device may include an opening into the second guidewire lumen in a lateral direction, and the method further includes mounting the closure device to the guidewire in a lateral direction prior to advancing the closure device over the guidewire.

Removing the dilator in a lateral direction may include tearing a portion of the dilator along a length of the dilator. The dilator may include an slot opening into the first guidewire lumen in a lateral direction, and the method further includes mounting the dilator to the guidewire in a lateral direction through the slot opening prior to advancing the closure device over the guidewire.

Additional advantages and novel features will be set forth in the description which follows or can be learned by those skilled in the art through reading these materials or practicing the examples disclosed herein. Some advantages of the invention can be achieved through the features recited in the attached claims.

BRIEF DESCRIPTION OF THE DRAWINGS

The accompanying drawings illustrate various embodiments of the present disclosure and are a part of the specification. The illustrated embodiments are merely examples and do not limit the scope of the invention.

FIG. 1 is a side view of an example wire assembly in accordance with the present disclosure.

FIG. 2 is a cross-sectional view of the wire assembly in FIG. 1 taken along cross-sectional indicators 2-2.

FIG. 2A is a cross-sectional view of another example wire assembly in accordance with present disclosure.

FIG. 3 is a cross-sectional view of the wire assembly of FIG. 2 taken along cross-sectional indicators 3-3.

FIG. 4 is a side view of a vascular closure assembly that includes the wire assembly of FIG. 1, a dilator, and a closure device, wherein the wire assembly is inserted into a vessel.

FIG. 5 is a cross-sectional view of the vascular closure assembly of FIG. 4 taken along cross-sectional indicators 5-5.

FIG. 10 is a side view of another example vascular closure assembly in accordance with the present disclosure.

FIG. 11 is a cross-sectional view of the vascular closure assembly of FIG. 10 taken along cross-sectional indicators 11-11.

FIG. 12 is a perspective view of another example closure device in accordance with the present disclosure.

FIG. 13 is a perspective view of another example closure device in accordance with the present disclosure.

FIG. 14 is a perspective view of another example dilator in accordance with the present disclosure.

Throughout the drawings, identical reference numbers designate similar, but not necessarily identical, elements.

DETAILED DESCRIPTION

Figure 6:
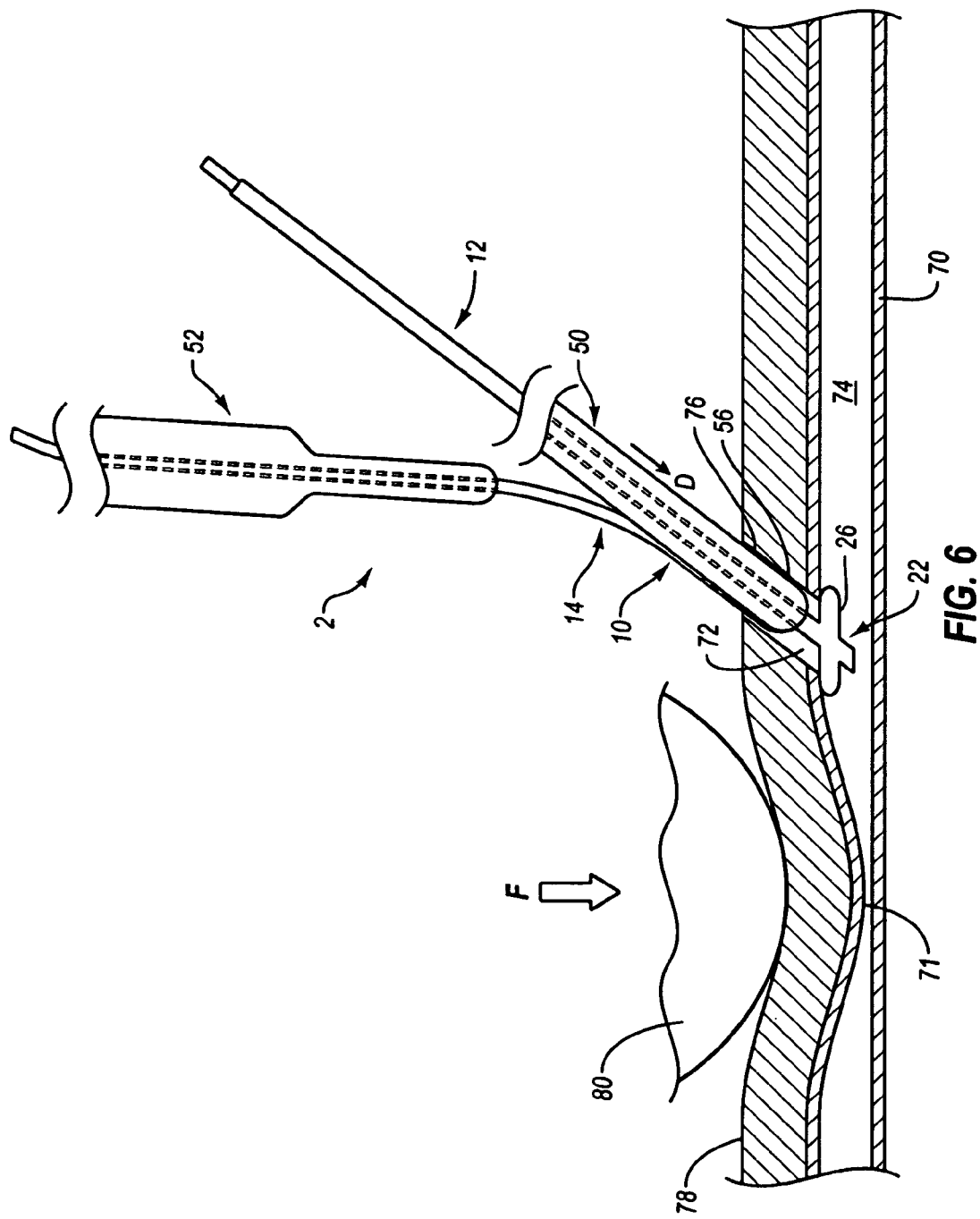
FIG. 6 is a side view of the vascular closure assembly of FIG. 4 with the dilator inserted into the tissue tract.

As mentioned above, vascular procedures are conducted throughout the world and require access to an vessel through a puncture. Most often, the vessel is a femoral artery. To close the puncture following completion of the procedure, many times a closure device is used to position a sealing plug within a percutaneous incision adjacent to the puncture. In some applications, a dilator is used to expand the percutaneous incision prior to positioning the sealing plug. The dilator and closure device may be advanced over a guidewire that is positioned extending through the percutaneous incision and puncture. The guidewire may include an anchor feature that is expandable within the vessel to provide a locating, anchoring, and/or sealing function internal the vessel, and returns to an unexpanded state for removal of the guidewire through the percutaneous incision and puncture after the sealing plug has been positioned in the percutaneous incision.

Guidewires used in such tissue closure procedures are typically in the range of about 20 cm to about 50 cm in length. Advancing the dilator and closure device over the guidewire to the percutaneous incision involves inserting a proximal end of the guidewire into a distal opening of the dilator and closure device at a location that is spaced relatively far from the percutaneous incision. Because of the relatively flexible nature of the guidewire and the distance from the percutaneous incision to the proximal end of the guidewire, the operator is typically required to use both hands when mounting the dilator and closure device to the guidewire. In some circumstances, both of the operator's hands may also be required to retract the dilator and closure device from off the proximal end of the guidewire.

The devices and methods of the present disclosure may provide the operator with the ability to advance and retract the dilator and closure device over the guidewire to treat the patient using one hand. The operator's other hand may be used to maintain pressure on the patient adjacent to the tissue tract, for example, to limit blood flow through a vessel of the patient being treated and to hold a distal end of the guidewire within the vessel being treated.

While the vascular instruments shown in the attached figures and described below include procedural sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the term "engage" and "engabable" are also used broadly to mean interlock, mesh, or contact between two devices. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

FIGS. 1-3 illustrate an example wire assembly 10 for use with a vascular closure assembly 2, as will be described in further detail below with reference to FIGS. 4-9. The wire assembly 10 includes first and second wire members 12, 14. The first and second wire members 12, 14 may be connected to each other at a connection point 16. The connection point 16 may be a single contact point between the first and second members 12, 14. Alternatively, the connection point 16 may extend along at least a portion of a length of each of the first and second wire members 12, 14. In alternative arrangements, multiple connection points may be provided at spaced apart locations along a length of the first and second wire members 12, 14. The connection provided between the first and second wire members 12, 14 by the connection point 16 provides for concurrent axial motion of the first and second wire members 12, 18.

Referring to FIG. 3, the connection point 16 results in the wire assembly 16 having an adjacent portion 18 wherein the first and second wire members 12, 14 are adjacent to each other, and a spaced apart portion wherein the first and second wire members 12, 14 are spaced apart in a lateral direction. The adjacent portion 18 may include contact between the first and second wire members 12, 14. The adjacent portion 18 may include the connection point 16. In some arrangements, the adjacent portion 18 may include providing the first and second wire members 12, 14 adjacent to each other in the lateral direction while remaining out of contact with each other.

The first and second wire members 12, 14 may have cross-sectional shapes that increase or decrease the amount of potential contact between outer surfaces of the first and second wire members 12, 14 along the adjacent portion 18. FIG. 2 illustrates the first wire member 12 having a generally circular cross-sectional shape and the second wire member 14 having a contoured, crescent cross-sectional shape. FIG. 2A illustrates an alternative wire assembly arrangement 110 wherein the first wire member 12 has a generally circular cross-sectional shape and a second wire member 114 has a general circular cross-sectional shape. The crescent cross-sectional shape of the second wire member 14 may provide for increased contact or potential contact between surfaces of the first wire member 12 and second wire member 14 as compared to the amount of contact or potential contact between the first wire member 12 and the second wire member 114 of the wire assembly 110.

The cross-sectional shape of the first and second wire members 12, 14 may influence the overall outer profile of the wire assembly 10. For example, the wire assembly 10 may have a smaller outer profile along the adjacent portion 18 as compared to the outer profile of the wire assembly 110 due at least in part to the cross-sectional shape and size of the second wire members 14, 114.

The first and second wire members 12, 14 may include various features that assist in positioning portions of the vascular closure assembly 2 relative to, for example, a tissue tract of a patient. The first wire member 12 includes some features that provide a locating function (i.e., the location of a vessel puncture in a vessel that is aligned with a tissue tract). In one example, the first wire member 12 includes a distal end portion 22, a proximal end portion 24, and an expandable anchor member 26. The first wire member 12 may also include a stop 28 positioned at the distal end portion 22 distal of the anchor member 26. First wire member 12 may further include an actuator member 30 in which an actuator wire 32 is positioned. The actuator wire 32 may include a distal end 34 that terminates at the anchor member 26, and an proximate end 36 that extends to the proximate end portion 24 of the first wire member 12.

In at least some arrangements, the first wire member 12 is operable to expand or contract the anchor member 26. In one example, the actuator wire 32 is operable to move axially within the actuator member 30 to move the anchor member 26 from the retracted state shown in solid line in FIG. 3 to the expanded state shown in broken line in FIG. 3. In some arrangements, the anchor member 26 is compressed against the stop 28 with the actuator wire 32 to created the anchor member's expanded state. Many different types of expandable anchors and associated mechanisms for actuating the expandable anchor are possible. An example expandable anchor member is disclosed in U.S. Application No. 61/238,297 entitled "Compressible Arteriotomy Locator for Vascular Closure Devices and Methods" filed on 31 Aug. 2009, which is incorporated herein in its entirety by this reference.

The anchor 26 is typically maintained in the unexpanded state shown in FIG. 3 while inserting the wire assembly 10 through a tissue tract and into, for example, a vessel via a vessel puncture. The anchor member 26 is actuated into an expanded state while on an opposing side of the tissue tract (i.e., within the vessel). The wire assembly 10 is retracted proximally to engage the expanded anchor member against a surface on the opposing side of the tissue tract (i.e., against an internal wall of the vessel adjacent to the vessel puncture), thus functioning as a locator and anchor while conducting treatment of the tissue tract. The expanded anchor member 26 may at least partially temporarily seal closed the tissue tract and vessel puncture. After the treatment of the tissue tract, the anchor member 26 is returned to the unexpanded state and the wire assembly is retracted proximally from the tissue tract.

The second wire member 14 may include a distal end portion 38 and a proximal end portion 40. The connection point 16 may be positioned at the distal end portion 38. The connection portion 16 may be positioned proximal of the anchor member 26.

Referring now to FIGS. 4-9, an example vascular closure assembly 2 is shown and described with reference to treatment of a vessel puncture 72 and tissue tract 76. The vascular closure assembly 2 (also referred to herein as a tissue puncture treatment device or a tissue puncture treatment assembly) includes the wire assembly 10 described above with reference to FIGS. 1-3, a dilator 50, and a closure device 52. The dilator 50 is mounted to the first wire member 12. The closure device 52 is mounted to the second wire member 14. The dilator 50 is configured to dilate the tissue tract 76 to a size sufficient to accommodate an unexpanded sealing pad of the closure device 52. The closure device 52 is configured to deliver the sealing pad to the tissue tract wherein the sealing pad is disposed to seal closed the tissue tract and vessel puncture. The dilator 50 includes a dilator wire lumen 54 and a distal end 56. The distal end 56 may be rounded to facilitate easier insertion into the tissue tract.

The closure device 52 includes a closure wire lumen 58, a sealing pad lumen 60, a sealing pad 62, and a distal end 64 (see FIG. 5). The closure wire lumen 58 and sealing pad lumen 60 are typically radially spaced apart from each other. In some arrangements, at least portions of the closure wire lumen 58 and sealing pad lumen 60 are open to each other. The sealing pad lumen 60 is usually separated from the closure wire lumen 58 so that the second wire member 14 remains out of contact with the sealing pad 62 while advancing and retracting the closure device 52 along the second wire member 14.

In other arrangements, the closure wire lumen 58 and sealing pad lumen 60 are formed as a single lumen. In one example, the second wire member 14 extends through a portion of the sealing pad 62. The sealing pad 62 may include a longitudinal slot that permits the second wire member 14 to exit from the sealing pad 62 in a lateral or radial direction. The sealing pad 62 may be positioned at the distal end 64 of the closure device 52 and have a length that is no greater than a length of a tissue tract into which the sealing pad is disposed.

In one example, the vascular assembly 2 is configured to treat a patient by sealing closed a vessel puncture 72 of a vessel 70 and a tissue tract 76 that provides access to the vessel puncture 72. The vessel 70 has a vessel interior 74 that is accessible through the vessel puncture 72 and tissue tract 76. The tissue has an outer surface 78. In at least one treatment method, an operator 80 applies a force F on the outer surface 78 that creates a collapsed portion 72 of the vessel 70 to reduce blood flow through the vessel 70. Typically, the collapsed portion 71 is created upstream of the vessel puncture 72 to minimize blood flow out of the vessel puncture 74 and tissue tract 76. Typically, the operator 80 (i.e., a portion of the hand of the operator) applies the force F to create the collapsed portion 71 prior to inserting the wire assembly 10 through the tissue tract 76 and vessel puncture 74 into the vessel interior 74. The operator maintains the applied force F on the patient to maintain the collapsed portion 71 of the vessel 70 until after the vessel puncture 72 and tissue tract 76 are sealed using the vascular closure assembly 2.

Because one hand of the operator is occupied applying the force F, the operator has only one remaining hand to operate the vascular closure assembly 2. The vascular closure assembly 2 includes features that make it possible for the operator to deploy the sealing pad 62 of the closure device 52 within the tissue tract 76 to seal close the tissue tract 76 and vessel puncture 72 using a single hand so that the operator's other hand can continue applying the force F to the patient.

The first and second wire members 12, 14 typically have a substantial length from the first ends 22, 38 to the second ends 24, 40, respectively. In some examples, the first and second wire members 12, 14 have a length of at least 30 cm. In most situations, it would be difficult for the operator to load the dilator 50 and closure device 52 onto a proximal end of a wire member that has a distal end inserted through the tissue tract 76 and vessel puncture 72 using only one hand. The dilator 50 is typically loaded onto a wire member by inserting a proximal end of the wire assembly (e.g., proximal end portion 24 of first wire member 12) into a distal open end of the dilator wire lumen 54. The closure device 52 is typically loaded onto a wire member by inserting a proximal end of the wire assembly (e.g., proximal end portion 40 of second wire member 14) into a distal end open end of the closure wire lumen 58. Due to the relatively small sizes of the wire member commonly used for tissue closure procedures, and the relatively small size of the wire lumens 54, 58, two hands are usually required to properly mount the dilator 50 and closure device 52 to the wire member (e.g., wire members 12, 14).

In at least some arrangements of the present disclosure, the construction of wire assembly 12 permits the dilator and closure device 50, 52 to be pre-mounted onto the first and second wire members 12, 14 prior to inserting the distal ends 22, 38 into the vessel 70 through the vessel puncture 72 and tissue tract 76. FIG. 4 illustrates the dilator 50 and closure device 52 advanced distally to a location relatively close to the outer surface 78 of the tissue outer surface 78. In some arrangements, the dilator 50 and closure device 52 are positioned within about 2 cm to about 20 cm from the tissue outer surface 78 prior to inserting the distal ends 22, 38 into the vessel 70. The dilator 50 and closure device 52 may be positioned at different distances relative to the tissue outer surface 78 at the initial stages of the method shown in FIG. 4 prior to using one of the dilator 50 and closure device 52 to treat the patient. The dilator 50 and closure device 52 are typically positioned a distance from the tissue tract 76 that permits the operator to advance and retract the dilator 50 and closure device 52 relative to the wire assembly 2 with one hand while maintaining the force F with a second hand.

Referring now to FIG. 5, the first wire member 12 is actuated to expand the anchor member 26 within the vessel interior 74. The wire assembly 10 is retracted proximally until the anchor member 26 contacts an inner surface of the vessel 70 adjacent to the vessel puncture 72. The operator typically feels a tactile resistance to further retraction in the proximal direction due to this contact of the anchor member 26 with the vessel 70. In at least some instances, such contact provides a "locating" function in which the operator receives a tactile indication of a position of the vessel puncture 72 relative to a feature of the closure device 2 (i.e., the anchor member 26). Typically, at least some tension in the proximal direction is maintained in the first wire member 12 during the following steps of treating the patient described with reference to FIGS. 6-8 until such time as the anchor member 26 is intentionally advanced distally out of contact with the vessel wall and actuated into the unexpanded state for removal from the patient.

After contact between the anchor member 26 and the vessel wall is obtained as shown in FIG. 6, the dilator 50 is advanced distally over the first wire member 12 into the tissue tract 76. The dilator 50 typically has an outer width dimension that is greater than an internal width dimension of the tissue tract prior to insertion of the dilator 50 into the tissue tract 76. Consequently, the dilator 50 tends to expand or dilate the tissue tract 76 to have a greater internal dimension.

The dilator 50 may be advanced over the first wire member 12 distally in the direction D up to the connection point 16. Positioning the connection point 16 as far distally as possible (i.e., up to a proximal side of the anchor member 26) can maximize the distance in which the dilator 50 travels distally within the tissue tract 76. In some arrangements, the dilator is configured to advance distally within the tissue tract 76 until contacting the anchor member 26.

Figure 7:
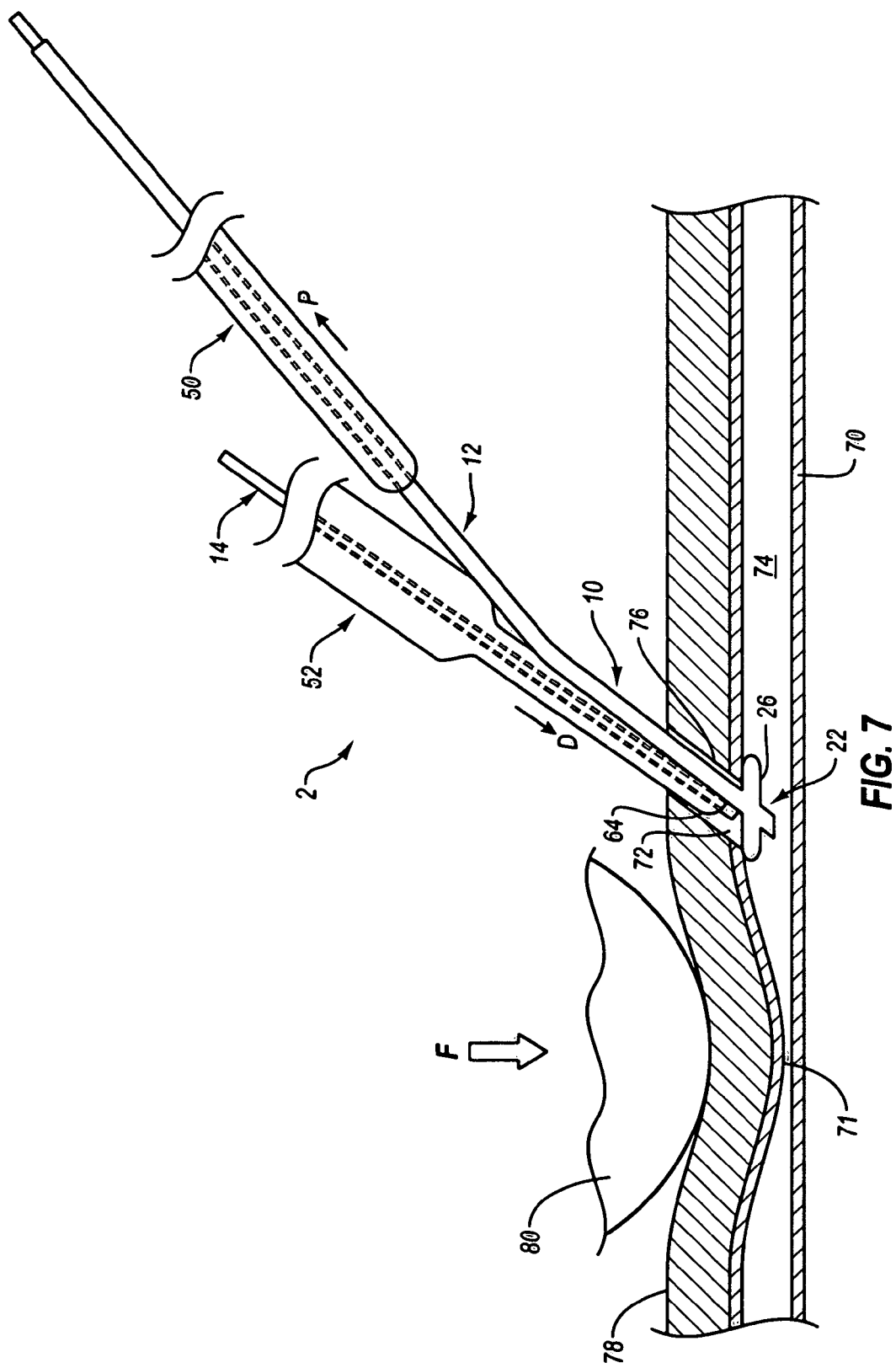
FIG. 7 is a side view of the vascular closure assembly of FIG. 4 with the closure device inserted into the tissue tract.
Figure 8:
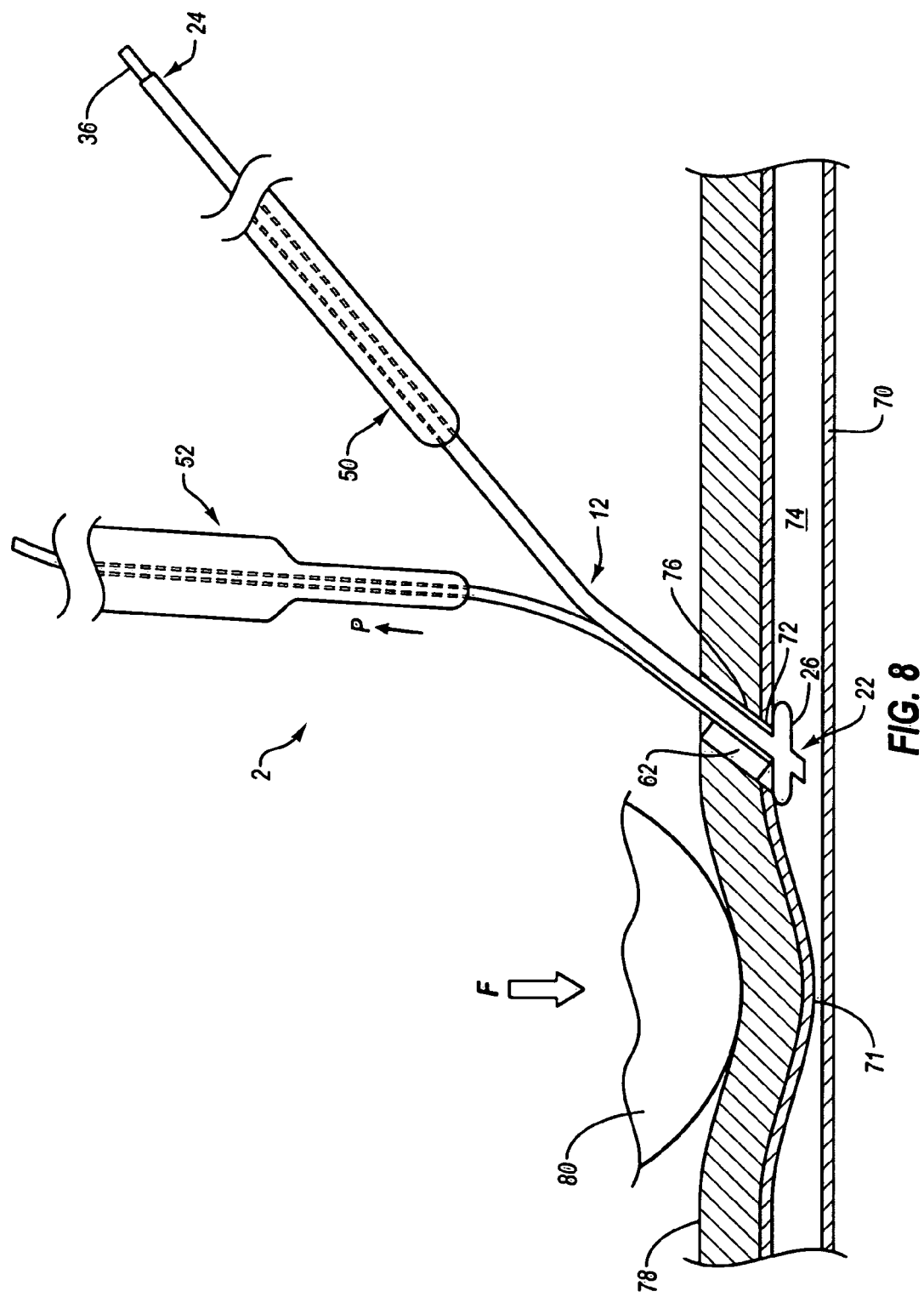
FIG. 8 is a side view of the vascular closure assembly of FIG. 4 with a sealing pad disposed in the tissue tract.

Referring now to FIG. 7, the dilator 50 is retracted in the proximal direction P a distance from the tissue outer surface 78 a distance sufficient to permit advancing the closure device 52 in the distal direction D over the second wire member 14 into the tissue tract 76. If desired, the dilator 50 can be retracted proximately until removed from off of the first wire member 12. In some examples, the predetermined retracted distance of the dilator 50 from the tissue outer surface 78 is in a range of about 5 to about 20 cm measured from the distal end 56 to the tissue outer surface 78 adjacent to the entrance into the tissue tract 76.

The closure device 52 is advanced distally in the direction D into the tissue tract 76. In some examples, the closure device 52 is advanced distally until the distal end 64 reaches the connection point 16. In some arrangements, the closure device 52 is configured to extend distally within the tissue tract 76 until contacting the anchor member 26. With the closure device 52 advanced to a desired position within the tissue tract 76, the closure device 52 is actuated to deploy the sealing pad 62 within the tissue tract 76. An example closure device and an associated sealing pad for use with the wire assembly 10 is disclosed in U.S. Patent Application No. 61/238,297.

After disposing the sealing pad 62 in the tissue tract 76, the remaining portions of the closure device 52 are retracted proximately in the direction P out of the tissue tract 76. The closure device 52 can be retracted a predetermined distance from the tissue outer surface 76. The predetermined distance may be, for example, in the range of about 5 to about 20 cm, or in some instances, about the same distance that the dilator 50 is retracted.

The first wire member 12 is actuated to return the anchor member 26 to an unexpanded state that permits withdrawal of the first wire member 12 from the vessel 70, through the vessel puncture 72, and through the tissue tract 76 adjacent to the sealing pad 62. Typically, the wire assembly 10 is configured and sized when the anchor member 26 is in an unexpanded state to permit removal from the tissue tract 76 without substantially altering a position of the sealing pad 62 within the tissue tract 76.

Figure 9:
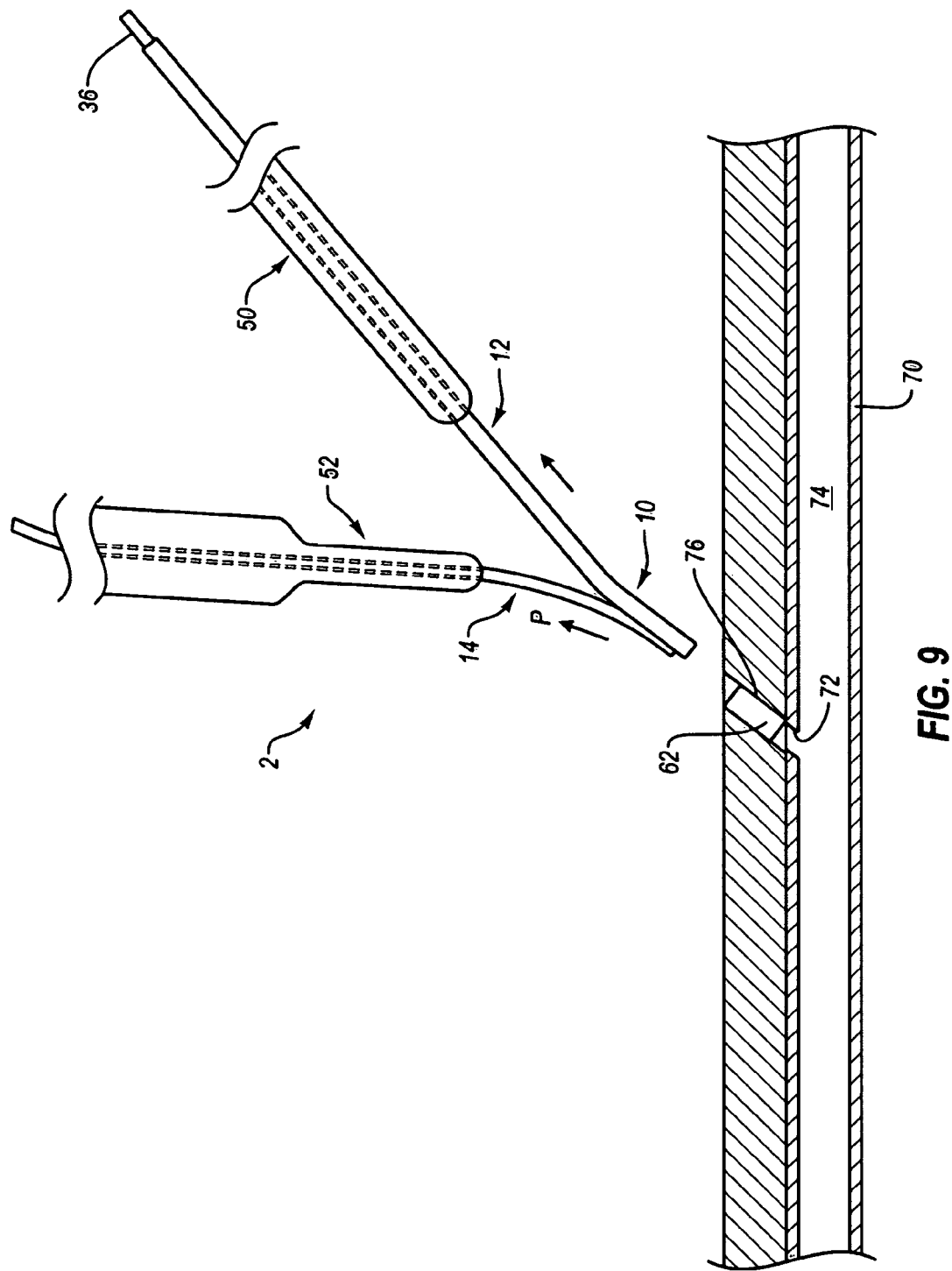
FIG. 9 is a side view of the vascular closure assembly of FIG. 8 with the sealing pad expanded in the tissue tract and the vascular closure assembly removed from the tissue tract.

FIG. 9 illustrates the wire assembly 10 retracted proximally out of the tissue tract 76 with the sealing pad 62 remaining disposed within the tissue tract 76. The sealing pad 62 may absorb fluid (i.e., blood), which absorption results in at least some expansion of the sealing pad 62 within the tissue tract 76. Expansion of the sealing pad 62 may provide sealing of at least one of the vessel puncture 72 and tissue tract 76. Expansion within the tissue tract 76 may create an outward force against internal walls of the tissue tract 76 that helps maintain a position of the sealing pad 62. The operator may remove the force F applied to the tissue surface 78 to permit unobstructed flow of blood in the vessel 70.

Referring now to FIGS. 10 and 11, another example vascular closure assembly 202 is shown and described. Vascular closure assembly 202 includes a first wire member 12, a dilator 250, and a closure device 52. The wire member 12 includes distal and proximal end portions 22, 24 and an expandable anchor member 26. The anchor member 26 is expandable from an unexpanded state shown in FIG. 10 to an unexpanded state shown in broken line in FIG. 10. The anchor member 26 may act as a locator when treating a patient that assists in, for example, locating an exit of a tissue tract. The anchor member 26 may be actuated back to an unexpanded state for removal from the tissue tract.

The dilator 250 includes a dilator wire lumen 254, a distal end 256, a perforation portion 255, and a wire side opening 257. The dilator 250 may be mounted to the wire member 12 by inserting the proximal end portion 24 into an open end of the dilator wire lumen 54. The proximal end portion 24 is advanced out of the wire side opening 257 at a location spaced between the distal end 256 and an proximal end 253 of dilator 250. The perforation portion 255 may extend from the distal end 256 to the wire side opening 257. The perforation portion 255 may provide for creation of an opening to be formed in the dilator 50 that extends from the dilator wire lumen 254 to an outer surface of the dilator 250 and extends along the length of the dilator 50 between the distal end 256 and the wire side opening 257.

The perforation portion 255 may be defined as a single perforation in the dilator 250. Alternatively, the perforation portion 255 may be defined as two or more perforations formed in the dilator 250. In some arrangements, the perforation portion 255 may be defined as a reduced thickness portion between the outer surface of the dilator 250 and the dilator wire lumen 254 that permits relatively easy tearing or opening up of the side wall of the dilator 250 to occur between the distal end 256 and the wire side opening 257. The opening up of the dilator 250 along the perforation portion 255 permits removal of the wire member 12 from within the dilator wire lumen 254 in the lateral direction without retracting the dilator 250 in the distal direction off of the proximal end 24 of the wire member 12. Removal of the dilator 250 from the wire member 12 in this way may provide advantages relating to treatment of a tissue tract with a single hand of the operator (i.e., the other hand of the operator that is not being used to apply pressure to the patient's tissue outer surface to reduce blood flow).

FIG. 10 illustrates the dilator 250 positioned at a location along the wire member 12 between the distal and proximal ends 22, 24. The closure device 52 is also mounted to the wire member 12 at a location between the distal and proximal ends 22, 24 and at a location proximal of the position of the dilator 250. After the dilator 250 is advanced distally into the tissue tract to dilate the tissue tract, the dilator 250 may be retracted out of the tissue tract and then removed from the wire member 12 by applying a force in the lateral direction to tear the dilator 250 along the perforation portion 255. With the dilator 250 removed from the wire member 12, the closure device 252 may then be advanced distally into the tissue tract wherein the sealing pad is disposed. The closure device 52 is then retracted proximately out of the tissue tract and the wire member 12 is also retracted out of the tissue tract leaving behind the sealing pad 62 to seal closed the tissue tract.

In other arrangements, the dilator 250 may include a perforation portion 255 or similar structure that extends along the entire length of the dilator 250 from the distal end 256 to the proximal end 253. This dilator configuration may be void of a wire side opening (e.g., opening 257) at a location spaced between ends 256, 253. Removing the dilator from the wire member 12 may include tearing or otherwise opening the dilator 250 along at least a portion of the entire length of the dilator. The opening formed in the sidewall of the dilator along the length of the dilator may be referred to as a slot feature. In some arrangements, the closure device 52 may include a feature similar to the perforation portion 252 that permits removal of the wire member from at least a portion of the closure device 52 without removing the closure device 52 proximally off of the proximate end 24 to the wire member 12.

Referring now to FIGS. 12-14, other constructions for the dilator and closure device may be possible to permit mounting and dismounting of the dilator and closure device from the wire assembly. FIG. 12 illustrates another example closure device 352 that includes a closure wire lumen 258, a sealing pad lumen 360, a sealing pad 362, and a side opening slot 366. A side opening slot 366 may extend along at least a portion of the length of the closure wire lumen 358. The side opening slot 366 may have a minimum width that is less than a maximum internal width or dimension of the closure wire lumen 358. The closure device 352 may be mounted to a wire member of a wire assembly by inserting the wire member laterally through the side opening slot 366 into the closure wire lumen 358. The size and shape of the side opening slot 366 may provide insertion of the wire member into the closure wire lumen 358, while limiting exit of the wire member from the closure wire lumen 358 through the side opening 366. In other arrangements, the side opening slot 366 is sized and configured to permit insertion into and removal of a wire member relative to the closure wire lumen 358 via the side opening slot 366.

The side opening slot 366 may be configured in some arrangements to provide a "snap-fit" connection between the closure device 352 and the wire member. In some arrangements, the minimum width of the opening into the side opening slot 366 is less than a maximum width dimension of the wire member. As a result, the portions of the closure device 352 that define the side opening slot 366 expand outward in order for the wire member to pass through the side opening slot 366 into the closure wire lumen 358, and expand to permit removal of the wire member from the closure wire lumen 358 out through the side opening slot 366.

Referring to FIG. 14, another example dilator 350 may include a dilator wire lumen 354 and a side opening slot 357. The side opening slot 357 may have features and functionality similar to the side opening slot 366 of the closure device 352 described above with reference to FIG. 12.

FIG. 13 illustrates another example closure device 452 that includes a closure wire lumen 458, a sealing pad lumen 460, a sealing pad lumen 462, and a side opening slot 466. Side opening slot 466 may have similar features and functionality as described above related to the side opening slot 366. The sealing pad lumen 460 may have a shape and size that maximizes a size of the sealing pad 462 that is carried in the closure device 452. The sealing pad lumen 460 is shown having a generally crescent shape cross-section that wraps at least in part around the closure wire lumen 458. The sealing pad 462 may have a similar crescent shape cross-section that mirrors the cross-sectional shape of the sealing pad lumen 460. The sealing pad 462 may have a greater cross-sectional area as compared to a cross-sectional area of a sealing pad having a circular cross-sectional shape for a closure device with a similar outer profile (i.e., compared to the closure device 352 of FIG. 12). Maximizing a size of a sealing pad of the closure device may be helpful in sealing the tissue tract.

The dilator and closure device features illustrated in FIGS. 12-14 may be used in combination with each other or in combination with any of the other dilator and closure device configurations disclosed in FIGS. 4-11. In some examples, the dilator is mounted to the second wire member 14 and the closure device is mounted to the first wire member 12. In other examples, the anchor member and anchor actuator features may be included with either or both of the first and second wire members.

Another example wire assembly includes first and second wire members that are integrally formed as a single piece. The wire assembly may include a single wire at a distal end that splits into first and second wire members to form a Y-shaped joint. The wire member may include, for example, a braided material that can be split into first and second portions while maintaining an integral structure.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure assembly, comprising:
a wire assembly including:
a first wire member having a distal end portion comprising a first length and a proximal end portion, the first wire member having a circular cross-sectional shape;
a second wire member having a distal end portion comprising a second length and a proximal end portion, the second wire member having a crescent cross-sectional shape that follows an outer contour of the circular cross-sectional shape of the first wire member;
wherein the first length and the second length are arranged side-by-side with each other and are fixedly connected to each other at a plurality of connection points along the first and second lengths, and the proximal end portion of the first wire member is arranged side-by-side with the proximal end portion of the second wire member wherein the proximal end portions are disconnected from each other;
a first device having a distal end portion, the first device being configured to advance over the first wire member, the distal end portion of the first wire member configured to advance through a lumen in the first device past the distal end portion of the first device;
a sealing pad deployable from a pad lumen in the first device, the sealing pad having a cross-sectional shape mirroring a cross-section of the pad lumen in the first device upon deployment from the pad lumen;
a second device configured to advance over the second wire member.

2. The tissue puncture locator device of claim 1 wherein the first device is a tissue closure device and the second device is a dilator.

3. The tissue puncture locator device of claim 1, wherein the first wire member has a first cross-sectional shape and the second wire member has a second cross-sectional shape that is different from the first cross-sectional shape.

4. The tissue puncture locator device of claim 1, wherein one of the first and second wire members includes an expandable anchor positioned at the distal end portion thereof, and an actuator member that extends from the anchor to the proximal end portion of thereof, the actuator member being operable to move the anchor between expanded and unexpanded states.

5. The tissue puncture locator device of claim 1, wherein the first device is operable to position the sealing pad within a percutaneous incision.

6. The tissue puncture locator device of claim 1, wherein the first device includes a first wire lumen, the pad lumen being radially spaced apart from the first wire lumen, and the second device includes a second wire lumen, the first and second wire lumens being configured to house the first and second wire members, respectively.

7. The tissue puncture closure assembly of claim 1, wherein the plurality of connection points comprise a side-by-side connection point extending along the first and second lengths.

8. The tissue puncture closure assembly of claim 1, wherein the plurality of connection points are spaced apart along the first and second lengths.

9. A tissue puncture closure assembly adapted for insertion into and sealing of a tissue puncture in an internal tissue wall that is accessible through a percutaneous incision, the device comprising:
a guidewire having a distal end and a proximal end, the distal end extending through the tissue puncture and percutaneous incision, the proximal end being spaced proximal of the percutaneous incision, the guidewire having first and second guidewire portions arranged side-by-side, the first guidewire portion having a circular cross-sectional shape, the second guidewire portion having a crescent cross-sectional shape, the first and second guidewire portions being fixedly connected to each other at a plurality of connection points along where they are side-by-side;

a closure device including a first guidewire lumen, a portion of the guidewire extending through the first guidewire lumen, the closure device having a sealing pad lumen, the sealing pad lumen having a lumen cross-sectional shape;

a sealing pad deployable from the sealing pad lumen of the closure device, the sealing pad having a pad cross-sectional shape mirroring the lumen cross-sectional shape upon deployment in the percutaneous incision;

a dilator including a second guidewire lumen, a portion of the guidewire extending through the second guidewire lumen, the dilator being configured to expand or dilate the percutaneous incision or tissue puncture;

wherein the closure device and the dilator are operable to advance over the guidewire for use within the percutaneous incision without retracting the closure device and dilator from the proximal end of the guidewire.

10. The tissue puncture closure device of claim 9, wherein the closure device and the dilator are operable to advance over the guidewire sequentially for use within the percutaneous incision.

11. The tissue puncture closure device of claim 9, wherein the first guidewire portion extends through the first guidewire lumen and the second guidewire portion extends through the second guidewire lumen.

12. The tissue puncture closure device of claim 11, wherein the first and second guidewire portions having different cross-sectional shapes.

13. The tissue puncture closure device of claim 9, wherein the guidewire includes an expandable anchor portion.

14. The tissue puncture closure device of claim 9, wherein the sealing pad lumen is arranged adjacent to the first guidewire lumen, the sealing pad being positioned within the sealing pad lumen.

15. The tissue puncture closure device of claim 14, wherein the second guidewire lumen is configured to have a closed state and an open state, wherein in the closed state the guidewire is retained within the dilator, and in the open state the guidewire is removable from the dilator prior to retracting the dilator from the proximal end of the guidewire.

16. The tissue puncture closure assembly of claim 9, wherein the plurality of connection points comprise a side-by-side connection point extending along where the first and second guidewire portions are side-by-side.

17. The tissue puncture closure assembly of claim 9, wherein the plurality of connection points are spaced apart along where the first and second guidewire portions are side-by-side.

* * * * *